(12) United States Patent
Lasswell et al.

(10) Patent No.: US 11,737,792 B2
(45) Date of Patent: Aug. 29, 2023

(54) SPINAL IMPLANT WITH BALL AND SOCKET JOINT HAVING MULTIPLE RADIUS TEAR SHAPED GEOMETRY

(71) Applicant: Spinal Simplicity, LLC, Overland Park, KS (US)

(72) Inventors: Timothy L. Lasswell, Burlington (CA); Parham Rasoulinejad, London (CA); John B. Medley, Fergus (CA)

(73) Assignee: Spinal Simplicity, LLC, Overland Park, KS (US)

( * ) Notice: Subject to any disclaimer, the term of this patent is extended or adjusted under 35 U.S.C. 154(b) by 552 days.

(21) Appl. No.: 16/821,525

(22) Filed: Mar. 17, 2020

(65) Prior Publication Data

US 2020/0214744 A1 Jul. 9, 2020

Related U.S. Application Data

(63) Continuation of application No. 16/010,626, filed on Jun. 18, 2018, now Pat. No. 10,624,678.

(60) Provisional application No. 62/645,520, filed on Mar. 20, 2018, provisional application No. 62/522,452, filed on Jun. 20, 2017.

(51) Int. Cl.
| | |
|---|---|
| *A61B 17/70* | (2006.01) |
| *A61F 2/44* | (2006.01) |
| *A61F 2/46* | (2006.01) |
| *A61F 2/30* | (2006.01) |

(Continued)

(52) U.S. Cl.
CPC ...... *A61B 17/7047* (2013.01); *A61B 17/7001* (2013.01); *A61B 17/7005* (2013.01); *A61B 17/7043* (2013.01); *A61B 17/7076* (2013.01); *A61F 2/4455* (2013.01); *A61F 2/4611* (2013.01); *A61B 17/7082* (2013.01); *A61B 2090/031* (2016.02); *A61F 2002/2835* (2013.01); *A61F 2002/30322* (2013.01); *A61F 2002/30538* (2013.01);
(Continued)

(58) Field of Classification Search
CPC ............ A61B 17/7047; A61B 17/7071; A61B 17/7043; A61B 17/7005; A61B 17/7032; A61B 17/7034; A61B 17/7035; A61B 17/7037; A61B 17/7056
See application file for complete search history.

(56) References Cited

U.S. PATENT DOCUMENTS 4,611,582 A * 9/1986 Duff .................. A61B 17/7007
606/260
4,901,964 A 2/1990 McConnell
(Continued)

OTHER PUBLICATIONS

D-G Huang et al., "Posterior atlantoaxial fixation: a review of all techniques," The Spine Journal, vol. 15, pp. 2271-2281 (2015).
(Continued)

*Primary Examiner* — Nicholas J Plionis
(74) *Attorney, Agent, or Firm* — Erise IP, P.A.

(57) ABSTRACT

A spinal implant configured to connect to a vertebra. The spinal implant comprises a ball and socket joint allowing poly-axial movement. The ball and socket joint includes a socket having a multiple radius tear drop geometry with a larger radius and a smaller radius, so that the ball can move freely within the larger radius of the socket until it is seated into the smaller radius of the socket upon locking of the ball and socket joint.

20 Claims, 10 Drawing Sheets

(51) Int. Cl.
    *A61B 90/00*      (2016.01)
    *A61F 2/28*       (2006.01)
(52) U.S. Cl.
    CPC .............. *A61F 2002/30622* (2013.01); *A61F 2002/30784* (2013.01); *A61F 2002/30841* (2013.01)

(56) References Cited

U.S. PATENT DOCUMENTS

| | | | |
|---|---|---|---|
| 5,074,864 A | 12/1991 | Cozad et al. | |
| 5,360,429 A | 11/1994 | Jeanson et al. | |
| 5,415,659 A | 5/1995 | Lee et al. | |
| 5,437,669 A | 8/1995 | Yuan | |
| 5,540,688 A | 7/1996 | Navas | |
| 5,620,444 A | 4/1997 | Assaker | |
| 5,928,232 A | 7/1999 | Howland | |
| 6,458,131 B1 | 10/2002 | Ray | |
| 7,686,833 B1 | 3/2010 | Muhanna et al. | |
| 8,790,380 B2 | 7/2014 | Buttermann | |
| 8,870,926 B2 | 10/2014 | Kumar | |
| 9,107,717 B2 | 8/2015 | Henderson, Sr. et al. | |
| 9,204,908 B2 | 12/2015 | Buttermann | |
| 9,775,650 B2 | 10/2017 | Buttermann | |
| 2003/0080267 A1* | 5/2003 | Eslick | F16B 2/065 248/229.1 |
| 2004/0087948 A1 | 5/2004 | Suddaby | |
| 2006/0241591 A1 | 10/2006 | Biscup | |
| 2007/0233091 A1 | 10/2007 | Naifeh et al. | |
| 2008/0103512 A1* | 5/2008 | Gately | A61B 17/7064 606/151 |
| 2008/0114401 A1 | 5/2008 | Liu | |
| 2008/0281423 A1 | 11/2008 | Sheffer | |
| 2009/0018584 A1 | 1/2009 | Henderson, Sr. | |
| 2009/0163920 A1 | 6/2009 | Hochschuler et al. | |
| 2011/0137353 A1 | 6/2011 | Buttermann | |
| 2011/0178552 A1 | 7/2011 | Biscup | |
| 2012/0265204 A1 | 10/2012 | Schmierer | |
| 2013/0090692 A1* | 4/2013 | Nuckley | A61B 17/7068 606/246 |
| 2013/0231704 A1 | 9/2013 | Larroque-Lahitette | |
| 2013/0274808 A1 | 10/2013 | Larroque-Lahitette | |
| 2014/0214083 A1 | 7/2014 | Refai | |
| 2015/0196328 A1* | 7/2015 | Hirschl | A61B 17/7056 606/279 |
| 2016/0015430 A1* | 1/2016 | Buttermann | A61B 17/7032 29/434 |
| 2016/0095632 A1* | 4/2016 | Faulhaber | A61B 17/7037 606/247 |
| 2016/0183981 A1 | 6/2016 | Schlaepfer | |
| 2017/0303970 A1 | 10/2017 | Puryear | |
| 2017/0319238 A1 | 11/2017 | Boehm, Jr. | |
| 2018/0008321 A1 | 1/2018 | Stern | |
| 2018/0289397 A1* | 10/2018 | Buttermann | A61B 17/7002 |

OTHER PUBLICATIONS

I. Dorward et al., "Seven Years of Experience With C2 Translaminar Screw Fixation: Clinical Series and Review of the Literature," Neurosurgery, vol. 68, No. 6, pp. 1491-1499 (Jun. 2011).
Olerud, "The C1 claw device: a new instrument for C1-C2 fusion," Eur. Spine J., vol. 10, pp. 345-347 (2001).
S.S Kale, "C1 C2 Fusion and Indication Technique and Complication," (2013).
J. Harms, "Posterior C1 C2 Fusion with Polyaxial Screw and Rod Fixation." Spine, vol. 26, No. 2, pp. 2467-2471 (2001).
S. Siasios, "C1-C2 Posterior Cervical Fixation by a Harms Technique Modification," J. Spinal Furg. 2017, vol. 4, No. 1, pp. 14-18.

* cited by examiner

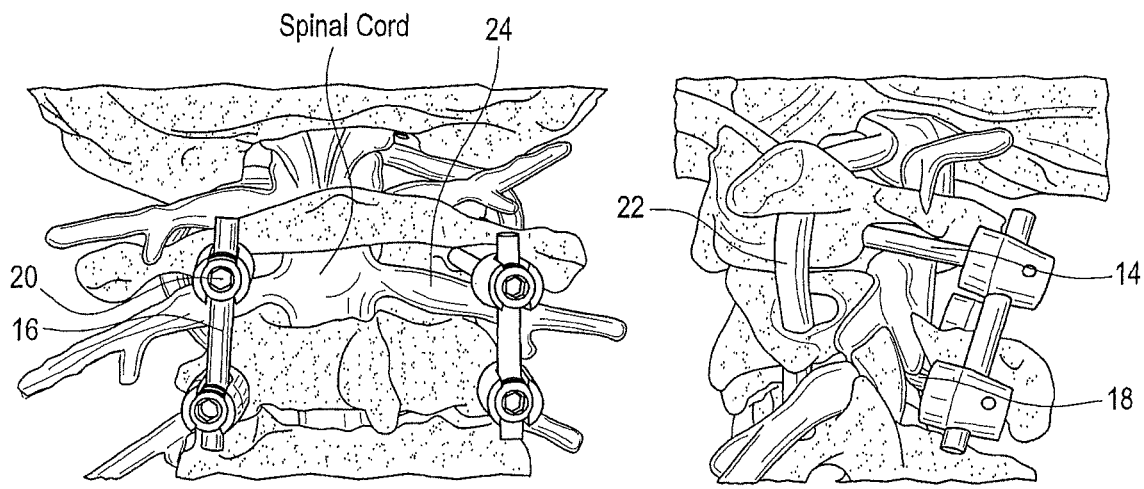
FIG. 2A
Prior Art
FIG. 2B
Prior Art
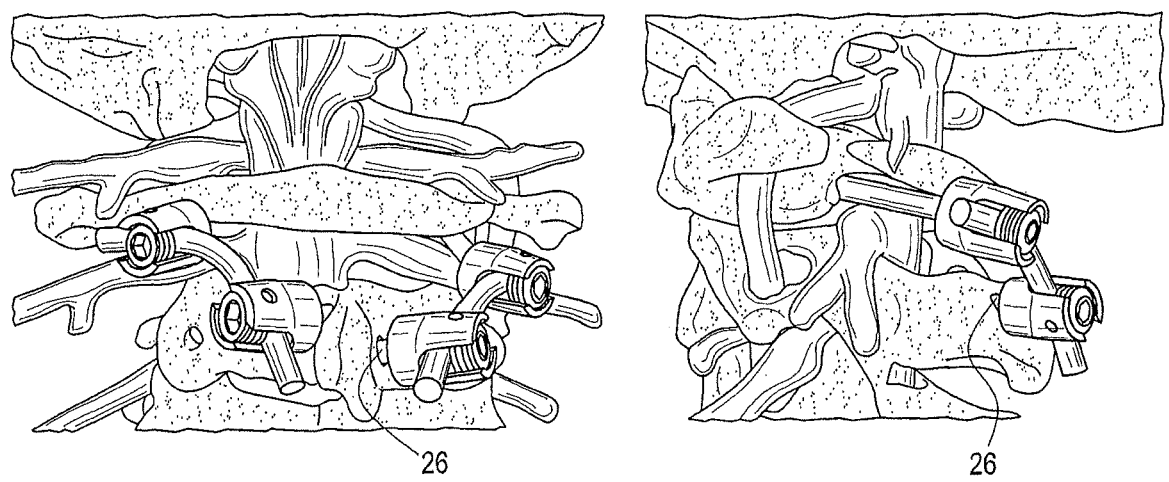
FIG. 3A
Prior Art
FIG. 3B
Prior Art

SPINAL IMPLANT WITH BALL AND SOCKET JOINT HAVING MULTIPLE RADIUS TEAR SHAPED GEOMETRY

CROSS REFERENCE TO RELATED APPLICATIONS

This is a continuation of U.S. patent application Ser. No. 16/010,626, filed Jun. 18, 2018, which claims priority from U.S. Provisional Application No. 62/522,452, filed on Jun. 20, 2017, and U.S. Provisional Application No. 62/645,520, filed on Mar. 20, 2018, the disclosures of which are hereby incorporated herein by reference in their entireties.

FIELD OF THE INVENTION

The present invention relates to the field of spinal fusion fixation devices. More particularly, the invention relates to a spinal fusion clamp implant that connects a first vertebra (e.g., the C1 vertebra) with a second vertebra (e.g., the C2 vertebra).

BACKGROUND OF THE INVENTION

The first and second cervical spine vertebrae (C1 and C2) are unique due to the presence of a synovial "pin joint" (referred to as the atlantoaxial joint), compared to the intervertebral discs in the lower cervical spine. As shown in FIG. 1A, the C2 vertebra 2 has a boney structure called the odontoid 4 which acts as the pin that sits within the ring of C1 vertebra 6. The odontoid 4 articulates against the anterior ring of C1 and is held in place by ligamentous structures. Atlantoaxial instability (AAI) occurs when there is excessive motion at the atlantoaxial joint most commonly caused by traumatic fracture of the odontoid. If left untreated, AAI can cause chronic pain, myelopathy and even death when even mild additional trauma is sustained to the destabilized joint segment. Odontoid fractures are classified into three types depending on the location of the fracture line in the C2 vertebra. Type II fractures, such as shown in FIG. 1B, are the most common and due to a higher risk of fracture non-union, surgical treatment is recommended. However, a surgical approach is not always possible, especially in the elderly patient population, due to concerns related to intraoperative blood loss, operating time, surgical invasiveness and recovery time. Given these concerns, only approximately 50% of the current elderly patient population is healthy enough to undergo surgery for AAI. Even when surgical treatment is possible, deciding the optimal treatment is not trivial and a common consensus has not yet been reached in clinical practice.

Posterior spinal fusion, in which an implant construct is used to hold adjacent vertebrae together until they heal into a single piece of solid bone, has become the most common surgical treatment for type II odontoid fractures in elderly patients when surgery is feasible. Since being introduced in 2001, the Harms construct has become the standard fixation for posterior fusion of the atlantoaxial segment due to good construct stability and high fusion rates.

FIGS. 2A and 2B show posterior and lateral views, respectively, of the use of the Harms construct in atlantoaxial fusion on a model of the upper cervical spine. The Harms construct consists of two polyaxial screws 14 that are inserted into the lateral masses 10 of C1, connected by titanium rods 16 to two additional polyaxial screws 18 that are inserted into the pedicles 12 of C2. Cap screws 20 are tightened down on the rods 16 to lock the construct in place and provide immediate stability to the joint until long term fusion occurs. The surgical procedure for implanting the Harms construct is very invasive, requiring a long incision and a dissection all the way down to the C1 lateral masses 10. The blood loss associated with this surgery tends to be very high due to disturbing the capillaries and venous plexus around the vertebral artery 22 and C2 nerve root 24. Additionally, placement of the C1 lateral mass screw 14 is risky due to the potential for injuring the vertebral artery 22 and often the C2 nerve root 24 is sacrificed to get a safer screw trajectory. Due to these surgical concerns, approximately half of the elderly patient population is not fit for surgery and must instead be treated conservatively with hard collar immobilization, ultimately leading to high fracture non-union rates and a permanent instability.

Attempts have been made both clinically and experimentally to develop new constructs and surgical techniques that better suit the needs of the C1/C2 segment. For example, Huang et al. (Posterior atlantoaxial fixation: a review of all techniques, *The Spine Journal*, Vol. 15, 2015, pp. 2271-2281) discusses, inter alia, various C1-C2 atlantoaxial stabilization/fixation techniques involving screws and clamps or hooks, such as C1-C2 apofix clamps, C1 hook combined with a C2 pedicle screw, and a C1 screw combined with C2 hooks. However, these techniques are not sufficiently stable (e.g., clamp slippage occurs frequently), result in pseudarthrosis, and/or are generally difficult to use in surgery. On the other hand, as shown in the posterior and lateral views of FIGS. 3A and 3B, respectively, and as reported in Dorward and Wright (Seven Years of Experience With C2 Translaminar Screw Fixation: Clinical Series and Review of the Literature, *Neurosurgery*, Vol. 68, No. 6, June 2011, pp. 1491-1499), C2 translaminar screws 26 have been used with excellent clinical success to replace C2 pedicle screws 18 in the Harms construct and thus eliminate the risk of a C2 screw injuring the vertebral artery 22. Although C2 translaminar screws 26 have reduced risk in posterior fusion procedures, the surgery remains equally invasive as the Harms procedure with regard to blood loss and operating time because of the continued use of C1 lateral mass screws 14.

It is therefore desirable to provide a spinal fusion fixation device that does not suffer from the above drawbacks.

Advantages of the present invention will become more fully apparent from the detailed description of the invention below.

SUMMARY OF THE INVENTION

The present invention in the various embodiments described below addresses the problems discussed above and other problems, by providing a spinal fusion clamp implant that connects a first vertebra with a second vertebra. The clamp implant includes a clamp assembly that connects to the first vertebra. The clamp assembly includes a superior jaw assembly having at least one superior jaw, and includes an inferior jaw assembly having at least one inferior jaw. The superior jaw and inferior jaw are opposedly arranged and clamp onto the first vertebra. The clamp implant also includes an implant assembly that connects to the second vertebra, and a connection system that connects the clamp assembly with the implant assembly. In a preferred embodiment, the first vertebra is the C1 vertebra, and the superior jaw and inferior jaw clamp onto the posterior arch of the C1 vertebra.

The present invention advantageously reduces the invasiveness of atlantoaxial posterior fusion surgeries by providing a clamp implant to replace C1 lateral mass screws and instead affix to the posterior arch of C1. Additional embodiments and additional features of embodiments for the clamp implant are described below and are hereby incorporated into this section.

BRIEF DESCRIPTION OF THE DRAWINGS

The features, objects, and advantages of the present disclosure will become more apparent from the detailed description set forth below when taken in conjunction with the drawings in which like reference characters identify correspondingly throughout and wherein:

FIG. 2A is an upper cervical spine anatomical model, posterior view, showing the Harms construct used in atlantoaxial fusion, and FIG. 2B is a lateral view of the same.

FIG. 3A is an upper cervical spine anatomical model, posterior view, showing a fusion construct that uses C2 translaminar screws, and FIG. 3B is a lateral view of the same.

DETAILED DESCRIPTION OF THE PREFERRED EMBODIMENTS

Figure 1A:
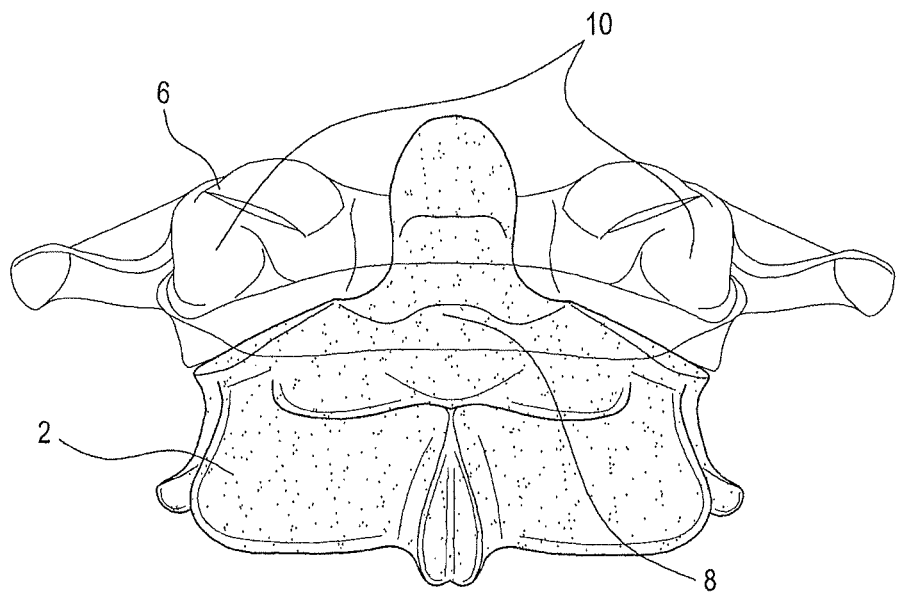
FIG. 1A shows the boney anatomy of the atlantoaxial joint (C1, partially transparent to show odontoid placement)
Figure 1B:
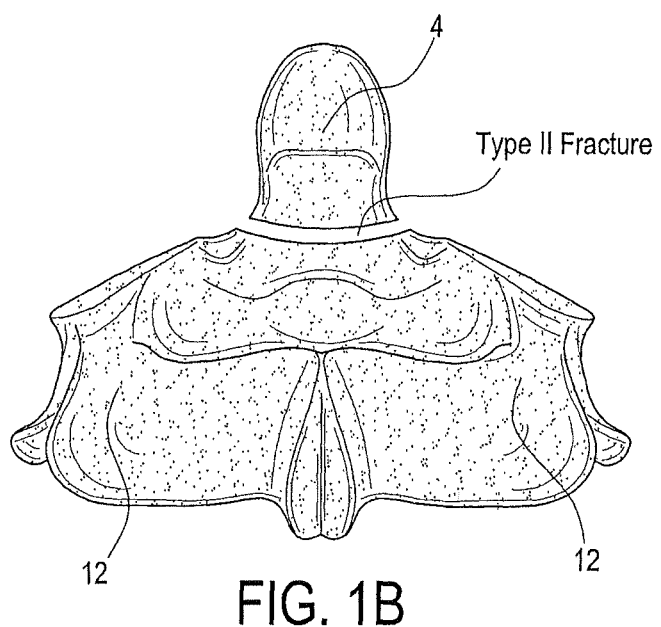
FIG. 1B is a view of the C2 vertebra showing a type II odontoid fracture.
Figure 4A:
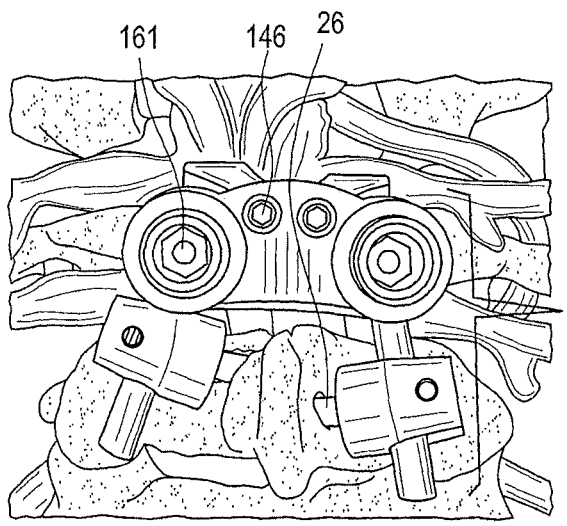
FIG. 4A is a posterior view of the clamp implant of the present invention used with C2 translaminar screws.
Figure 4B:
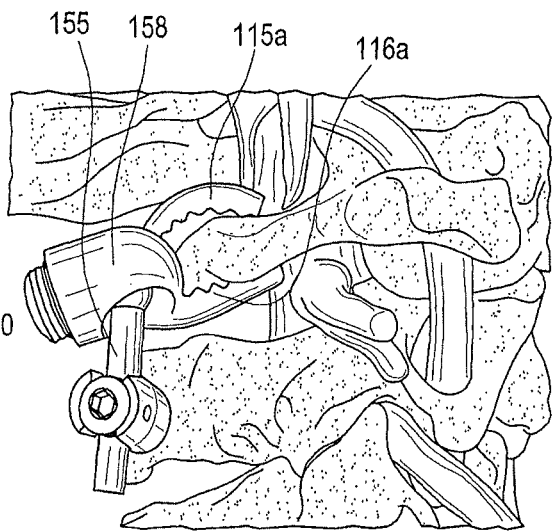
FIG. 4B is a lateral view of the clamp implant used with C2 translaminar screws.
Figure 4C:
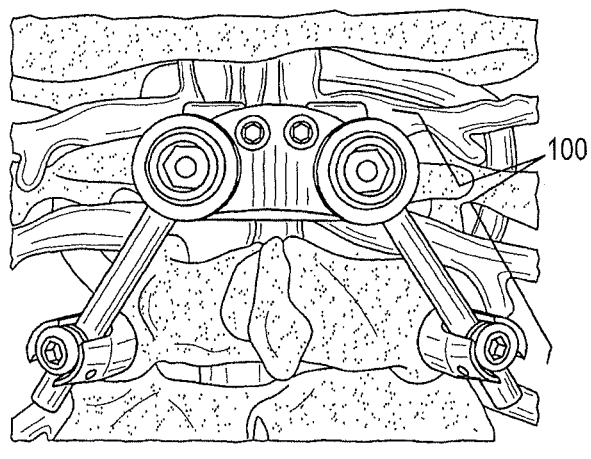
FIG. 4C is a posterior view of the clamp implant used with C2 pedicle screws.
Figure 4D:
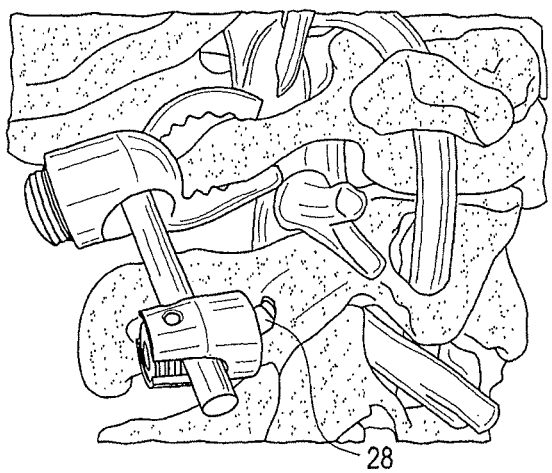
FIG. 4D is a lateral view of the clamp implant used with C2 pedicle screws.

In the following detailed description, reference is made to certain embodiments. This detailed description is merely intended to teach a person of skill in the art further details for practicing preferred aspects of the present teachings and is not intended to limit the scope of the claims. Therefore, combinations of features disclosed in the following detailed description may not be necessary to practice the teachings in the broadest sense, and are instead taught merely to describe particularly representative examples of the present teachings. It is to be understood that other embodiments may be employed and that various structural changes may be made.

With reference to FIGS. 4A-9C, the present invention is directed to a clamp implant 100 configured to connect a first vertebra (preferably the C1 vertebra 6) with a second vertebra (preferably the C2 vertebra 2). The clamp implant 100 comprises: (i) a clamp assembly 110 (FIG. 6A) configured to connect to the C1 vertebra 6, (ii) an implant assembly, such as translaminar screws 26 or pedicle screws 28, to connect to the C2 vertebra 2, and a connection system 150 that connects the clamp assembly 110 with the implant assembly, i.e., translaminar screws 26 or pedicle screws 28.

Clamp assembly 110 comprises a superior jaw assembly 115 of two superior jaws 115a, and an inferior jaw assembly 116 of two inferior jaws 116a. The superior jaws 115a and the inferior jaws 116a are opposedly arranged and are configured to clamp onto the posterior arch 8 of the C1 vertebra 6. The jaws of the clamp are concave in shape to conform to the superior and inferior sides of the C1 posterior arch. The fixation surface of the inferior jaw 116a is designed with less concavity (i.e., greater radius of curvature) than the superior jaw 115a, since the inferior side of the C1 posterior arch is generally flatter than the superior side. In different implant variations, the concavity of the inferior and superior jaws may be the same. Alternatively, the inferior and superior jaws may also be designed to have no concavity (i.e, be flat) or may even be designed to have a variety of convex shapes.

Figure 5A:
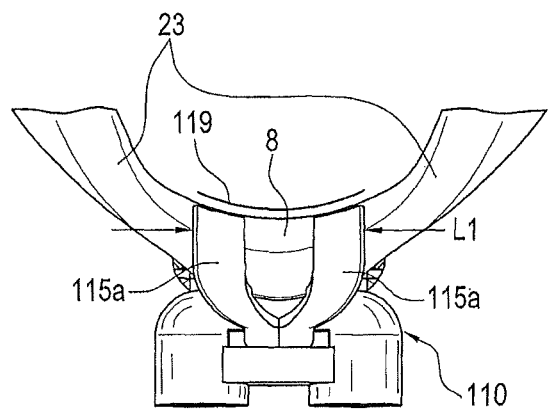
FIGS. 5A and 5B are superior and inferior axial views, respectively, of the clamp implant on the C1 posterior arch (polyaxial rods and rod cap screws omitted).
Figure 5B:
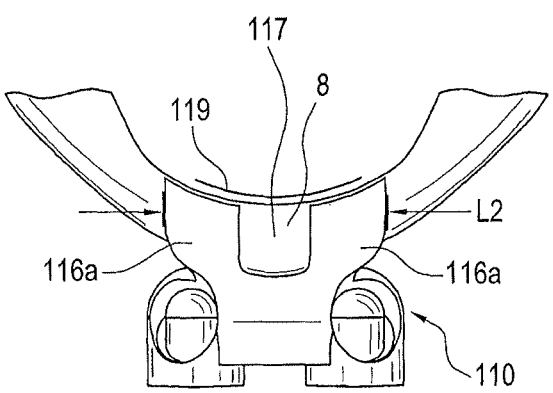

As shown in FIGS. 5A and 5B, the inferior jaw assembly 116 has a cutout 117 in the midsection which acts as a window for bone graft material to promote long term fusion. The superior jaw assembly 115 has two parts to enhance its grip on the C1 posterior arch 8 that may be slightly non-symmetrical in its anatomical geometry, as described in further detail below. The gap between the two parts of the superior jaw assembly 115 may also act as a window for bone graft material. In an alternative embodiment, the inferior jaws 116a can have no bone graft cutout, creating a single, slightly stiffer, inferior jaw. This single inferior jaw can also be smaller in width to effectively create a three pronged (rather than the current four pronged) clamp that could allow bone graft materially to be placed on the lateral sides of the jaw rather than the medial sides.

To avoid injury to the vertebral artery 22 (which sits atop the vertebral groove 23), the lateral footprint distance $L_1$ of the superior jaws 115a is less than the lateral footprint distance $L_2$ of the inferior jaws 116a. Injury to the vertebral artery 22 is not a concern for the inferior jaws 116a, so the $L_2$ dimension can be larger to provide additional component stiffness which increases overall implant stability. In different implant variations, the $L_1$ and $L_2$ dimensions could vary, and $L_1$ may not be smaller than $L_2$.

As further shown in FIGS. 5A and 5B, respectively, in the axial (horizontal) plane, the clamp jaws are designed to have a curved cutout 119 that follows the C1 posterior arch so that the implant does not protrude into the spinal canal. Optionally, rounded edges can be added to these curved cutouts to further reduce the risk of pointed objects near the spinal canal.

Figure 6A:
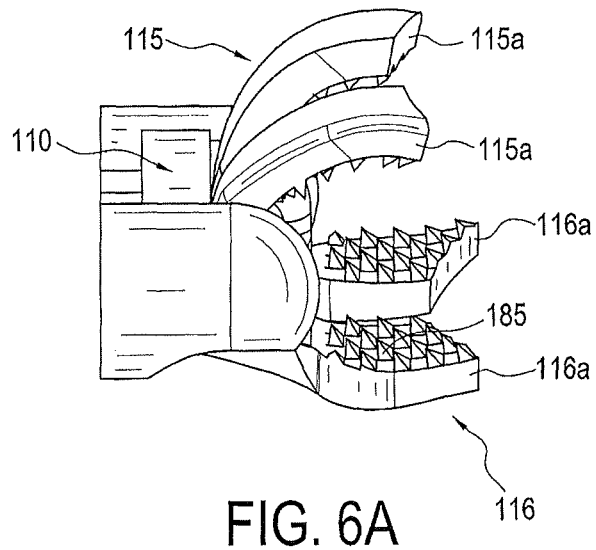
FIG. 6A is a side profile of the clamp implant, showing the saw tooth surface for bone fixation
Figure 6B:
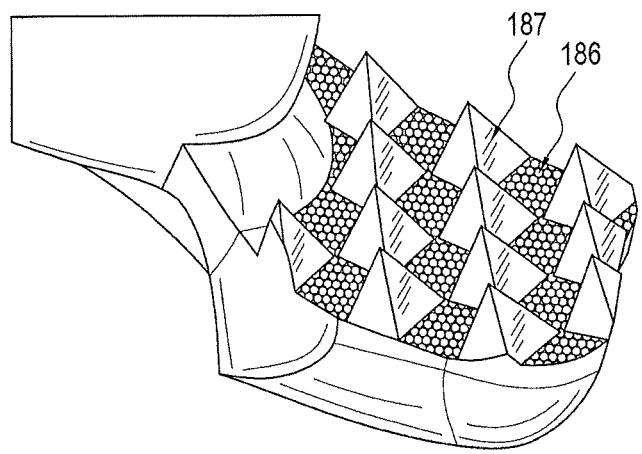
FIG. 6B shows the detail of the spiked teeth of the jaws, and the porous material between the teeth.

As shown in FIG. 6, the superior jaws 115a and the inferior jaws 116a preferably have a saw tooth surface 185. The saw tooth design prevents the implant from backing out in the posterior direction. Movement in the anterior direction is not a concern since the body of the clamp butts up against the C1 posterior arch 8. In different embodiments of this design, the jaw surface may consist of cylindrical spikes, pyramid spikes, a knurled surface or a porous surface. Such surfaces (including the saw tooth surface 185) may produce bone strains that bioactively encourage bone ongrowth/ingrowth. A combination of jaw surfaces may also be used, such as the case shown in FIG. 6B, where porous surface regions 186 are positioned between spike tips 187. The porous surface regions can be created as part of a three dimensional printing method of fabricating the clamp component or by temporarily attaching a metal powder to the surface regions and then sintering it to provide a permanent fused porous surface structure or by using a plasma spraying technique with a metal powder. Additionally, the jaw surface can include a material attached to it (including porous regions) that helps promote bone ongrowth/ingrowth biochemically, such as hydroxyapatite or hydroxyapatite with tricalcium phosphate. All of the above described jaw surfaces help the jaws grip the C1 posterior arch 8 to minimize or eliminate movement (e.g., micromotion) between the jaw surface and bone of the C1 posterior arch from the time of surgery until the bony fusion is established, thus enhancing overall implant stability.

Figure 7D:
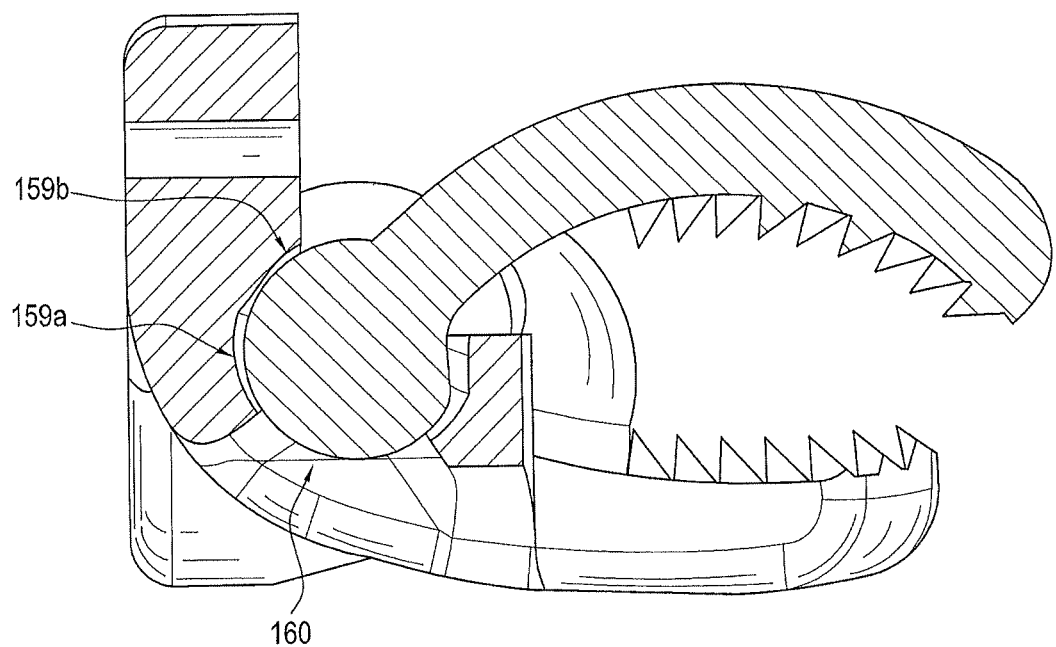
FIG. 7D shows the multiple radius tear drop geometry of the socket, and a cutout in the socket.
Figure 7A:
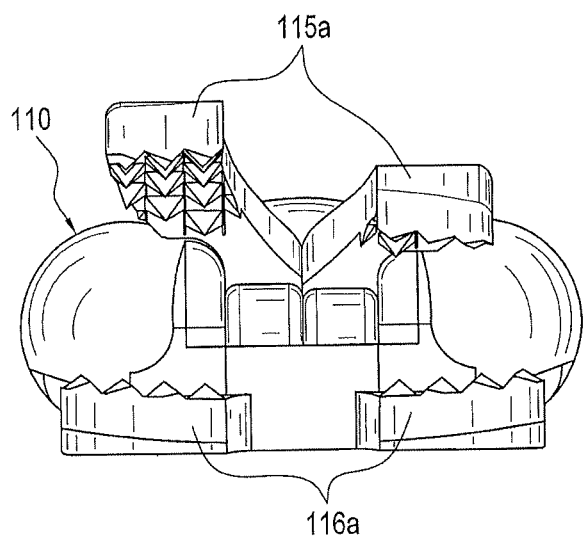
FIGS. 7A is an anterior view of the implant showing independent jaw articulation.

As shown in the anterior view of FIG. 7A, the two superior jaws 115a are designed to both articulate and be locked independently of each other. This allows the implant to adapt to non-symmetric anatomy and still achieve adequate fixation. To provide articulation, the superior jaw assembly 115 may comprise a (linear) single axial joint 131 (see FIGS. 7A and 7B) associated with each of the superior jaws 115a. The single axial joint 131 allows for single axial movement of the superior jaw 115a with respect to the corresponding inferior jaw 116a. Alternatively, the superior jaw assembly 115 may include a ball joint 133 (see FIG. 7C) associated with each of the superior jaws 115a. Each ball joint 133 allows for multi-axial movement of the associated superior jaw 115a with respect to the corresponding inferior jaw 116a. The ball joint geometry allows for additional degrees of motion and a better fit between the implant and the posterior arch of C1. Additive manufacturing techniques can be used to manufacture this ball joint as a one step process with no assembly required. In this case, relief cut-outs (or windows) 160 may be included in the socket of the ball joint geometry to allow for the escape of un-sintered powder (see FIG. 7D). The socket of the ball joint may also comprise a multiple radius tear drop geometry, with a larger radius 159a and a smaller radius 159b, in order to allow more clearance between the ball and socket during the additive manufacturing process while still allowing a tight clearance when the ball is seated in the locked position. Standard assembly and manufacturing techniques using CNC's, lathes, precision grinding and precision tooling may also be used to create the ball joint.

Figure 7B:
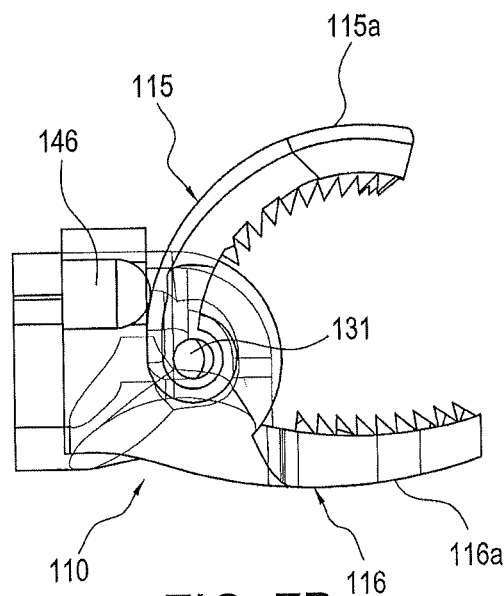
FIG. 7B is a side detail of the implant showing the jaw locking mechanism (clamp body and inferior jaw is shown partially transparent)
Figure 7C:
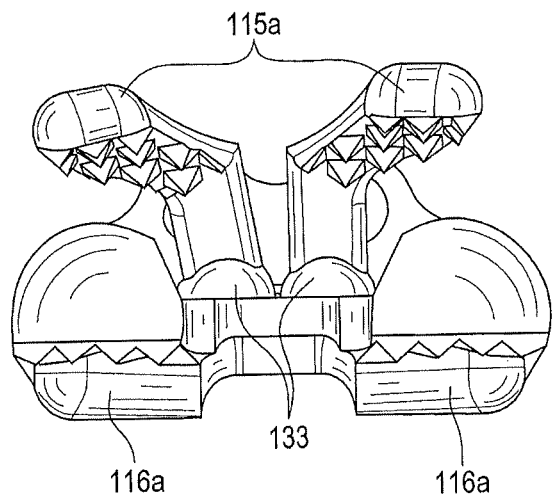
FIG. 7C shows the ball joint geometry to allow additional degrees of freedom for jaw motion.

The superior jaw assembly 115 further includes jaw locking screws 146 (see FIGS. 7B and 8B-8D) that can be tightened to lock the superior jaws 115a in place after the implant has been placed on the C1 posterior arch 8 and fitted to the anatomy. The clamp body has two threaded holes to allow for placement of the jaw locking screws 146. A buttress thread may be used to prevent loosening of the locking screws. As shown in FIG. 7B, the top surface of the jaws that come in contact with the jaw locking screws 146 are designed to act as cam surfaces that provide progressive closing of the jaws as the jaw locking screws 146 are tightened. The ends of the jaw locking screws 146 are rounded to promote a smooth sliding motion as the jaws 115a close. Tightening of the jaw locking screws 146 also controls the clamping pressures at the jaw/bone fixation interfaces. In other embodiments of this design, the jaw locking screws 146 can be in line with the center of rotation of the jaws and simply act as set screws. The clamping pressure of the jaws 115a can then be controlled by external tooling, such as pliers, placed around the jaws. Alternatively, one jaw locking screw (instead of two) could be placed centrally in the body of the clamp to lock both jaws simultaneously.

Alternatively or additionally, in a likewise manner to that described above, the two inferior jaws 116a may be designed so they are capable of independent movement from each other. Thus, the inferior jaw assembly 116 may comprise a (linear) single axial joint (not shown) similar to single axial joint 131 associated with the inferior jaws 116a, or a ball joint (not shown), similar to ball joint 133 associated with the inferior jaws 116a. The inferior jaw assembly 116 would then further comprise jaw locking screws (not shown), similar to jaw locking screws 146, for locking the inferior jaws 116a in place.

As described in further detail below, an implant assembly, such as C2 translaminar screws 26 or pedicle screws 28, is configured to be implanted into translaminar portions or pedicle portions of the C2 vertebra (see FIGS. 4A-4D and 9A-9C).

Figure 8A:
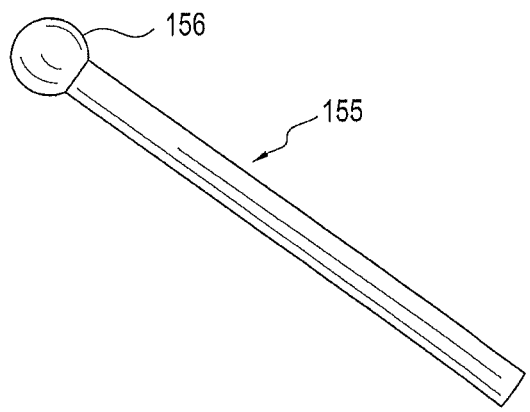
FIG. 8A shows the polyaxial rod of the present invention with a spherical head.
Figure 8B:
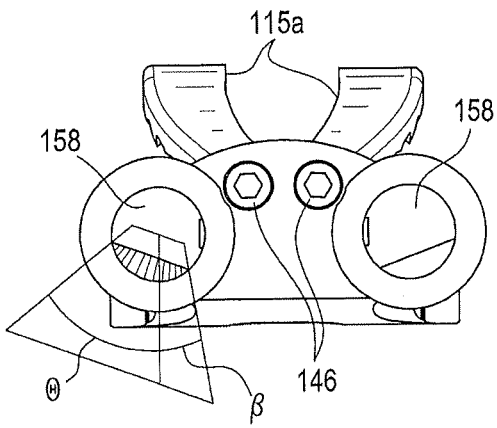
FIG. 8B shows the socket articulation for the polyaxial rod.
Figure 8C:
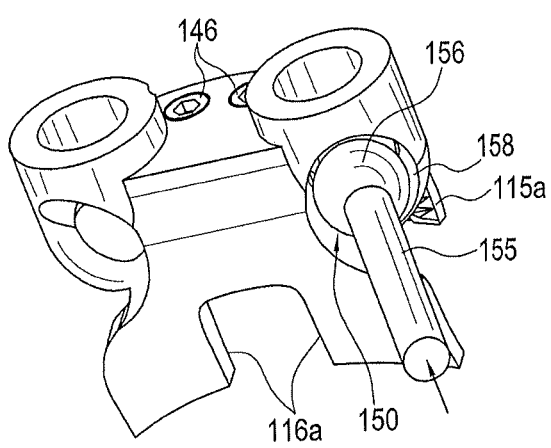
FIG. 8C shows the polyaxial rod insertion into the clamp body.
Figure 8D:
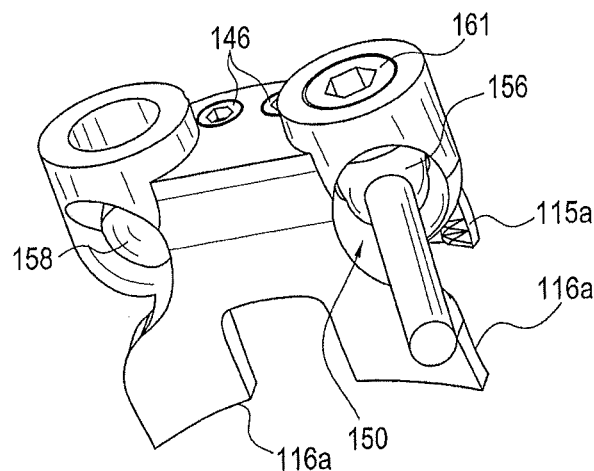
FIG. 8D shows the locking of the polyaxial rod into the socket by tightening the rod cap screw.

Connection system 150 comprises a polyaxial connection system comprising a polyaxial rod 155 with a spherical head 156, and a rod cap screw 161 configured to be tightened to apply pressure to the spherical head 156, thereby locking the polyaxial rod 155 in place. More specifically, once the clamp 110 has been locked into place on the C1 posterior arch 8, rods 155 are inserted into the clamp to connect the clamp 110 to the implant used in C2, thus creating the overall clamp implant fusion construct. The use of C2 pedicle screws 28 and/or C2 translaminar screws 26 has been previously discussed as feasible implant components that could be used in conjunction with the C1 clamp 110. However, the C1 clamp 110 can be used with any C2 implant component designed to be connected to the C1 implant component through the use of rods. As shown in FIG. 8A, the rods for the C1 clamp (referred to as polyaxial rods 155) have spherical heads so that, prior to tightening of the rod cap screw 161, they can articulate within the polyaxial sockets 158 of the C1 clamp body. The sockets, shown in FIGS. 8C and 8D, are designed to allow ±30° of rod rotation in any direction. Sockets 158 have a bias and allow more rotation in the lateral direction (0) and less rotation in the medial direction (p), as shown in FIG. 8B, to provide a better fit when pedicle screws are used in C2. As shown in FIG. 7D, sockets 158 can also have additional windows or cutouts 160 and/or holes to improve the aesthetic appearance of the device as well as reduce the overall bulk of the device. The posterior regions of the sockets are threaded to allow for the rod cap screws 161 to be tightened into place. A buttress thread may be used to prevent loosening of the rod cap screws. The polyaxial rods 155 are inserted through the bottom of the clamp body (FIG. 8C) and then slid forward into the sockets when the rod cap screws 161 are threaded into place (FIG. 8D). The rods 155 are specifically designed to be inserted in the bottom of the clamp body so that a fully threaded hoop can be maintained for the rod cap screws. This full hoop minimizes deformation due to the splaying generated during thread tapping and rod cap screw tightening. In another embodiment, slots or cutouts are provided in the sockets to allow the rods to be inserted from the posterior and/or lateral directions.

Figures 9A, 9B:
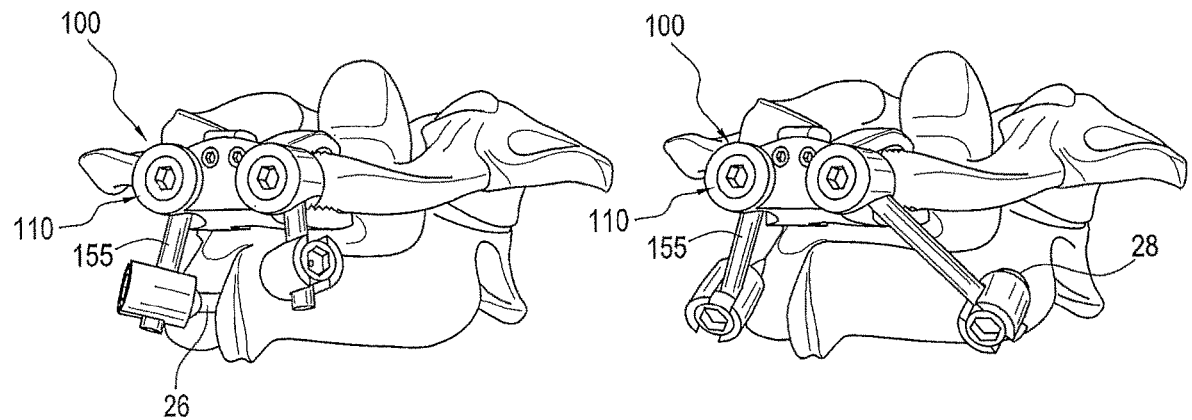
FIG. 9A shows the final fusion construct created with the C1 clamp implant and C2 translaminar screws.
FIG. 9B shows the final fusion construct created with the C1 clamp implant and C2 pedicle screws.

Once both rods 155 are placed in the sockets 158, they can be connected to the C2 implant assembly, such as C2 translaminar screws 26 (FIG. 9A) or C2 pedicle screws (FIG. 9B). Tightening down all of the rod cap screws 161 then locks the clamp implant into place and creates a stable fusion construct.

Figure 9C:
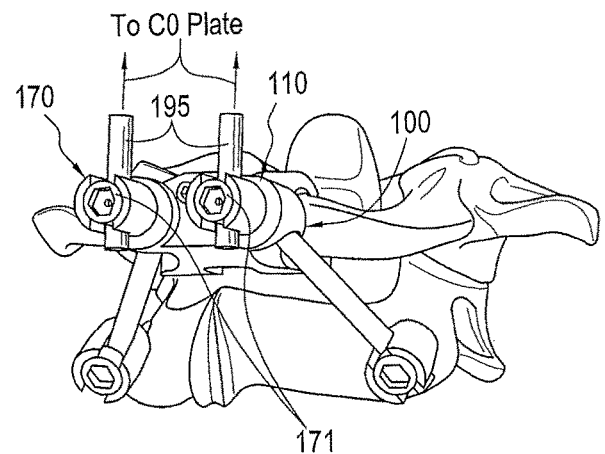
FIG. 9C shows the final fusion construct created with the C1 clamp, C2 pedicle screws and a C0 plate.

The clamp implant of the present invention can also be modified for a multi-level fusion that includes the occipital (C0) vertebra. In this case, the rod cap screws 161 are replaced with rod cap screws that also have polyaxial fixation heads 170 (FIG. 9C). Standard cervical rods 195 can then be attached to these polyaxial heads 170 (via tightening of polyaxial set screws 171) and connected to a C0 vetebra plate (not shown). Additionally, the construct can be extended below C2 by using longer polyaxial rods. These rods may be non-linear to allow better alignment with the rest of the patient anatomy and/or cervical instrumentation. The extended construct may allow for the implant to be fixed to a vertebra different than (or in addition to) the C2 vertebra (e.g., the C3 vertebra). Fixation of the implant to another vertebra may employ similar or different implantation techniques as those described in this disclosure for the C2 vertebra.

The clamp implant of the present invention is manufactured from a biocompatible material such as pure titanium, titanium alloy, stainless steel or cobalt chromium alloy or a material with potential for bone ongrowth/ingrowth such as porous tantalum. Alternatively, or additionally, porous surfaces with or without coatings such as hydroxyapatite or hydroxyapatite with tricalcium phosphate can be used on parts of the implant to bioactively encourage bone ongrowth/ingrowth. Some parts of the clamp implant of the present invention can also be made from a polymer such as PEEK or a polymer composite such as carbon fiber reinforced PEEK. Ceramic inserts can be used for some of the bearing surfaces.

Figure 10:
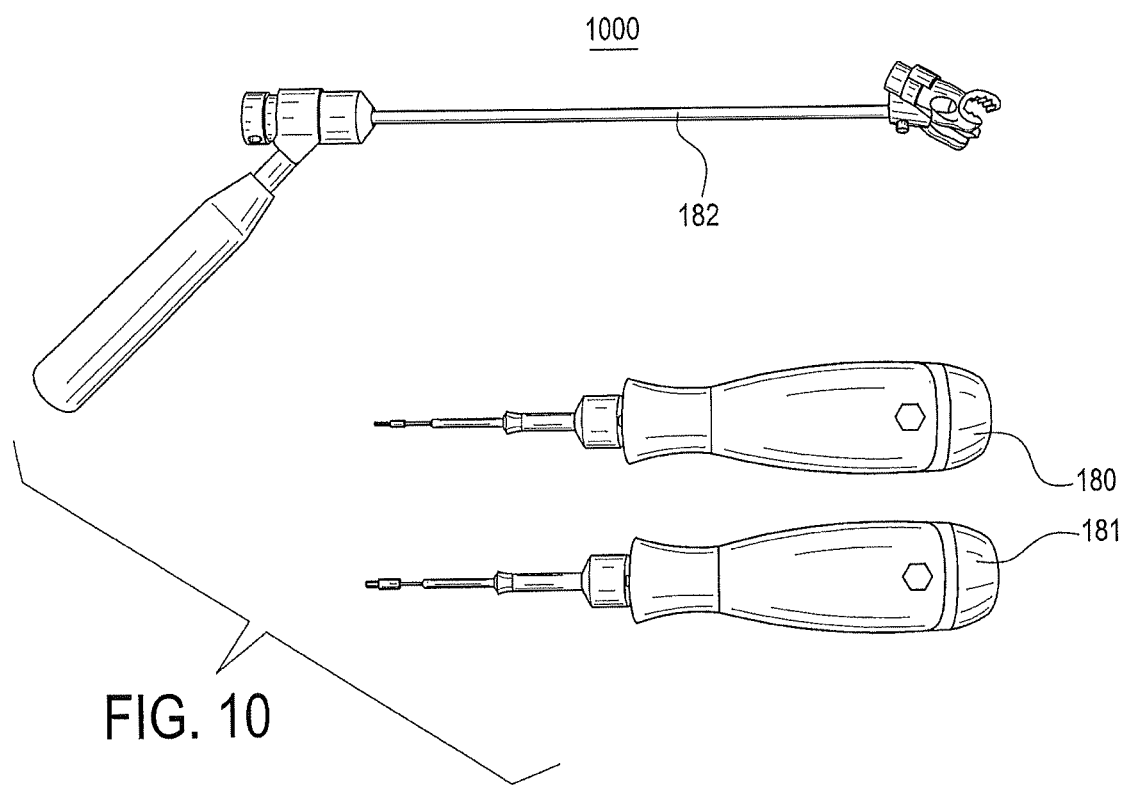
FIG. 10 shows the instrumentation used in conjunction with the implant of the present invention.
Figure 11A:
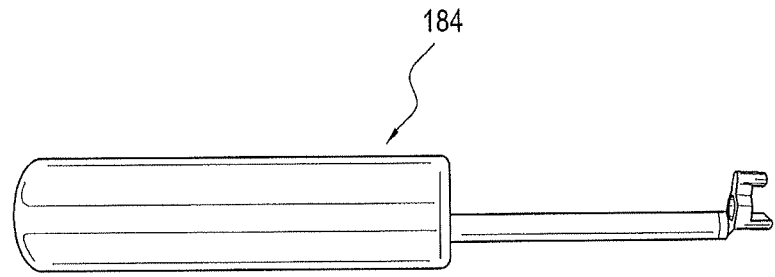
FIG. 11A shows an alternative inserter tool with an axial handle and no angular offset.
Figure 11B:
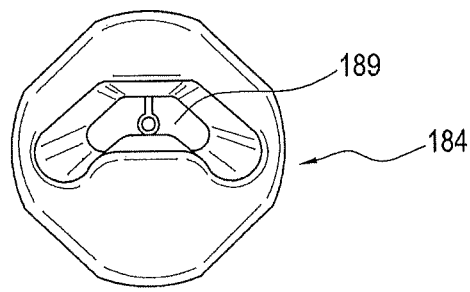
FIG. 11B shows an end view of the alternative inserter tool with a window in the handle for screwdriver access.
Figure 11C:
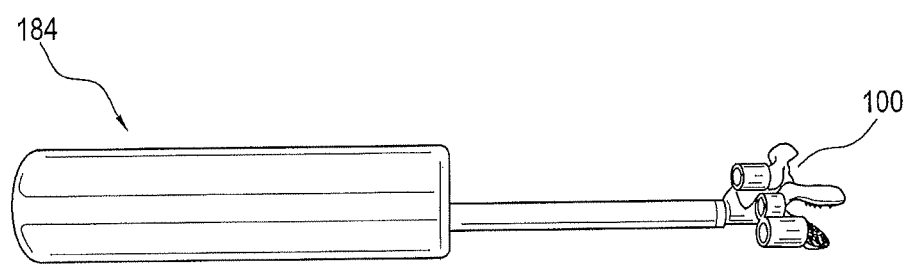
FIG. 11C shows the alternative inserter tool with the clamp implant attached to the distal end of the tool.

The instrumentation 1000 used in conjunction with the implant, shown in FIG. 10, consists of two torque limited screwdrivers 180, 181 and an inserter tool 182. The implant is first placed on the inserter tool through the use of clips, screws, latches or an interference fit. While on the inserter tool, the jaws of the implant may be kept open using clips or latches or through the use of springs and wires that may consist of a Nitinol mechanism. The jaws may also be kept open by a frictional interference fit between the ball and socket geometry 133 previously described. The shaft of the inserter tool can have an angular offset to allow for better visualization of the posterior arch during insertion of the implant. Alternatively, an inserter tool 184 with an axial handle and no angular offset as shown in FIG. 11A may be used. In this case, the handle of the inserter tool will have a plurality of through holes or one larger window 189, shown in FIG. 11B, to allow for the torque screwdrivers to access the locking screws. The inserter tool 182, 184, with clamp implant 100 mounted on the tool (FIG. 11C), is then used to place the implant on the posterior arch of C1 and hold it in place until the jaw locking screws are tightened down. During the tightening of the jaw locking screws, the inserter tool 182, 184 also acts as the counter torque device. Once the jaws are tight, the inserter tool may be used to reduce fractures (if a fracture is present) and/or obtain ideal alignment at the fusion stage before inserting the full construct of the clamp implant. This reduction or fracture alignment is done while the inserter tool is still connected to the implant, allowing the handle of the inserter tool to provide better leverage on re-positioning C1. The inserter tool 182 is then removed to free up space for the remainder of the full construct, i.e., screws 26, 28 to be implanted in C2, and connection system 150. Upon final tightening of the polyaxial rods 155, the inserter tool 182, 184 can once again be used as a counter torque device.

The clamp implant of the present invention can be provided in a variety of sizes to cater to the anatomy of the entire patient population. Three-dimensional printing may be used to fabricate any or all of the components in the manufacture of the clamp implant. Three-dimensional printing may also be used to introduce porosity or a lattice structure to encourage bone ingrowth/ongrowth.

Although embodiments are described above with reference to a clamp implant comprising a clamp assembly that, for example, clamps onto the posterior arch of C1, the jaw assemblies of the clamp assembly described in any of the above embodiments may alternatively clamp onto other portions of C1 or other vertebra. Such alternatives are considered to be within the spirit and scope of the present invention, and may therefore utilize the advantages of the configurations and embodiments described above.

In addition, although embodiments are described above with reference to a clamp implant comprising an implant assembly (e.g., for C2), the implant assembly described in any of the above embodiments may alternatively be replaced with a secondary clamp assembly (e.g., of the types used for C1 described above). The jaw assemblies for this secondary clamp assembly may clamp onto any portion of the C2 or other vertebra. Such alternatives are considered to be within the spirit and scope of the present invention, and may therefore utilize the advantages of the configurations and embodiments described above.

The above description and drawings are only to be considered illustrative of specific embodiments, which achieve the features and advantages described herein. Modifications and substitutions to specific process conditions may be made. Accordingly, the embodiments of the invention are not considered as being limited by the foregoing description and drawings.

More generally, even though the present disclosure and exemplary embodiments are described above with reference to the examples according to the accompanying drawings, it is to be understood that they are not restricted thereto. Rather, it is apparent to those skilled in the art that the disclosed embodiments can be modified in many ways without departing from the scope of the disclosure herein. Moreover, the terms and descriptions used herein are set forth by way of illustration only and are not meant as limitations. Those skilled in the art will recognize that many variations are possible within the spirit and scope of the disclosure as defined in the following claims, and their equivalents, in which all terms are to be understood in their broadest possible sense unless otherwise indicated.

The invention claimed is:

1. A unitary spinal implant for implanting at a spine, wherein the spine presents a generally longitudinal axis, the spinal implant comprising:

a first clamp assembly comprising a first superior jaw and a first inferior jaw connected together by a first ball joint,
   wherein the first clamp assembly is for mounting to a first portion of a single vertebra;
a second clamp assembly comprising a second superior jaw and a second inferior jaw connected together by a second ball joint,
   wherein the second clamp assembly is for mounting to a second portion of the single vertebra generally opposite of the first portion of the single vertebra along an axis generally transverse to the longitudinal axis of the spine;
a clamp body forming a base portion connecting the first clamp assembly and the second clamp assembly adjacent to each other,
   wherein the first clamp assembly and the second clamp assembly are configured to open and close independently from each other;
a first locking screw received within the clamp body,
   wherein an end of the first locking screw contacts an outer surface of the first superior jaw,
   wherein rotation of the first locking screw advances the first locking screw along the outer surface of the first superior jaw to close the first clamp assembly on the single vertebra; and
a second locking screw received within the clamp body,
   wherein an end of the second locking screw contacts an outer surface of the second superior jaw,
   wherein rotation of the second locking screw advances the second locking screw along the outer surface of the second superior jaw to close the second clamp assembly on the single vertebra.

2. The spinal implant of claim 1,
wherein the clamp body comprises a first hole for receiving the first locking screw therein and a second hole for receiving the second locking screw therein,
wherein the first locking screw controls articulation of the first clamp assembly and the second locking screw controls articulation of the second clamp assembly.

3. The spinal implant of claim 2,
wherein the end of the first locking screw and the end of the second locking screw are rounded in shape to promote a smooth sliding motion when the first locking screw advances along the outer surface of the first superior jaw and when the second locking screw advances along the outer surface of the second superior jaw.

4. The spinal implant of claim 3,
wherein the outer surface of the first superior jaw acts as a cam surface for the first locking screw such that the rotation of the first locking screw provides progressive clamping of the first superior jaw on the single vertebra,
wherein the outer surface of the second superior jaw acts as a cam surface for the second locking screw such that the rotation of the second locking screw provides progressive clamping of the second superior jaw on the single vertebra.

5. The spinal implant of claim 1,
wherein the first inferior jaw has less concavity than the first superior jaw, and the second inferior jaw has less concavity than the second superior jaw, such that the first clamp assembly and the second clamp assembly are configured to conform to a C1 posterior arch.

6. The spinal implant of claim 1,
wherein at least one of the first ball joint and the second ball joint includes a socket having a multiple radius tear drop geometry.

7. The spinal implant of claim 1,
wherein the clamp body comprises at least one polyaxial socket configured to receive a polyaxial rod therein.

8. The spinal implant of claim 7,
wherein the at least one polyaxial socket comprises a first socket adjacent the first clamp assembly and a second socket adjacent the second clamp assembly.

9. The spinal implant of claim 7,
wherein the at least one polyaxial socket is accessible from an inferior side of the clamp body.

10. The spinal implant of claim 7, further comprising:
an opening cooperating with the at least one polyaxial socket and a rod cap screw received in the opening, said rod cap screw configured to lock a polyaxial rod in the at least one polyaxial socket.

11. The spinal implant of claim 1,
wherein an inner surface of at least one of the first superior jaw, the second superior jaw, the first inferior jaw, and the second inferior jaw comprises a textured surface for gripping bone.

12. The spinal implant of claim 1,
wherein an inner surface of at least one of the first superior jaw, the second superior jaw, the first inferior jaw, and the second inferior jaw comprises a porous surface for promoting bone ingrowth.

13. A unitary medical implant for implanting at vertebrae in a spine, wherein the spine presents a generally longitudinal axis, the implant comprising:
   a first top jaw and a first bottom jaw that cooperate together via a first ball joint to clamp a first portion of a single vertebra therebetween;
   a second top jaw and a second bottom jaw that cooperate together via a second ball joint to clamp a second portion of the single vertebra therebetween,
      wherein the second portion of the single vertebra is generally opposite of the first portion of the single vertebra along an axis generally transverse to the longitudinal axis of the spine;
   a clamp body having the first top jaw, the first bottom jaw, the second top jaw, and the second bottom jaw mounted thereto such that the first top jaw is adjacent to the second top jaw and the first bottom jaw is adjacent to the second bottom jaw;
   a first locking screw received within the clamp body,
      wherein an end of the first locking screw slidingly contacts an outer surface of the first top jaw,
      wherein rotation of the first locking screw slides the first locking screw along the outer surface of the first top jaw to close the first top jaw on the single vertebra; and
   a second locking screw received within the clamp body,
      wherein an end of the second locking screw slidingly contacts an outer surface of the second top jaw,
      wherein rotation of the second locking screw slides the second locking screw along the outer surface of the second top jaw to close the second top jaw on the single vertebra,
      wherein the first top jaw and the first bottom jaw are configured to open and close independently from the second top jaw and the second bottom jaw.

14. The medical implant of claim 13,
wherein the clamp body further comprises:
   a first socket adjacent the first bottom jaw for receiving a first rod therein; and a second socket adjacent the second bottom jaw for receiving a second rod therein.
15. The medical implant of claim 14, further comprising:
a first opening cooperating with the first socket for receiving a first rod cap screw therein; and
a second opening cooperating with the second socket for receiving a second rod cap screw therein.
16. The medical implant of claim 15, further comprising:
the first rod and the first rod cap screw configured to lock the first rod in the first socket; and
the second rod and the second rod cap screw configured to lock the second rod in the second socket.
17. The medical implant of claim 13,
wherein an inner surface of at least one of the first top jaw, the second top jaw, the first bottom jaw, and the second bottom jaw comprises a textured surface for gripping bone.
18. The medical implant of claim 13,
wherein an inner surface of at least one of the first top jaw, the second top jaw, the first bottom jaw, and the second bottom jaw comprises a porous surface for promoting bone ingrowth.
19. A method of performing spinal surgery comprising:
inserting a unitary spinal implant into a patient at a spine, wherein the spine presents a generally longitudinal axis, said implant comprising:
 a first clamp assembly comprising a first superior jaw and a first inferior jaw connected together by a first ball joint,
  wherein the first clamp assembly is for mounting to a first portion of a single vertebra;
 a second clamp assembly comprising a second superior jaw and a second inferior jaw connected together by a second ball joint,
  wherein the second clamp assembly is for mounting to a second portion of the single vertebra generally opposite of the first portion of the single vertebra along an axis generally transverse to the longitudinal axis of the spine;
 a clamp body connecting the first clamp assembly and the second clamp assembly adjacent to each other,
  wherein the first clamp assembly and the second clamp assembly are configured to open and close independently from each other;
rotating a first locking screw to close the first clamp assembly on a first vertebra of the patient; and
rotating a second locking screw to close the second clamp assembly on the first vertebra of the patient.
20. The method of claim 19, further comprising:
inserting a first polyaxial rod into a bottom of the clamp body adjacent the first inferior jaw;
connecting the first polyaxial rod to a second vertebra;
inserting a second polyaxial rod into a bottom of the clamp body adjacent the second inferior jaw; and
connecting the second polyaxial rod to the second vertebra.

\* \* \* \* \*